United States Patent [19]

Fujii et al.

[11] 4,257,940
[45] Mar. 24, 1981

[54] VALYLLEUCYLLYSINE DERIVATIVES, PROCESS FOR PRODUCING SAME AND METHOD FOR MEASURING ACTIVITY OF ENZYMES USING SAME

[75] Inventors: Setsuro Fujii, Toyonaka; Mamoru Sugimoto, Chiba; Takashi Yaegashi, Funabashi, all of Japan

[73] Assignee: Torii & Co., Ltd., Tokyo, Japan

[21] Appl. No.: 88,321

[22] Filed: Oct. 25, 1979

[30] Foreign Application Priority Data

Oct. 30, 1978 [JP] Japan .................... 53/133394

[51] Int. Cl.$^3$ .................... C07C 103/52; C12Q 1/00; C12Q 1/36
[52] U.S. Cl. .................... 260/112.5 R; 435/24; 435/4
[58] Field of Search .................... 260/112.5 R; 435/24, 435/4

[56] References Cited

U.S. PATENT DOCUMENTS 4,137,225  1/1979  Ekenstam et al. ............ 260/112.5 R

*Primary Examiner*—Delbert R. Phillips
*Attorney, Agent, or Firm*—Beveridge, DeGrandi, Kline & Lunsford

[57] ABSTRACT

A valylleucyllysine derivative represented by the formula,

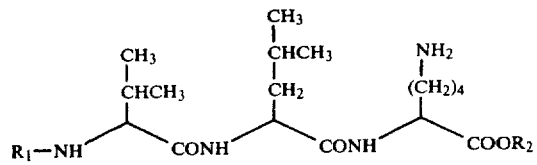

wherein $R_1$ represents hydrogen or benzoyl and $R_2$ represented naphthyl. The above compound is useful as an excellent substrate for various anzymes, such as, trypsin, plasmin, kallikrein, urokinase, Cl-esterase and the like. Accordingly, the activity of enzymes can be measured by use of said compound as a substrate.

3 Claims, 2 Drawing Figures

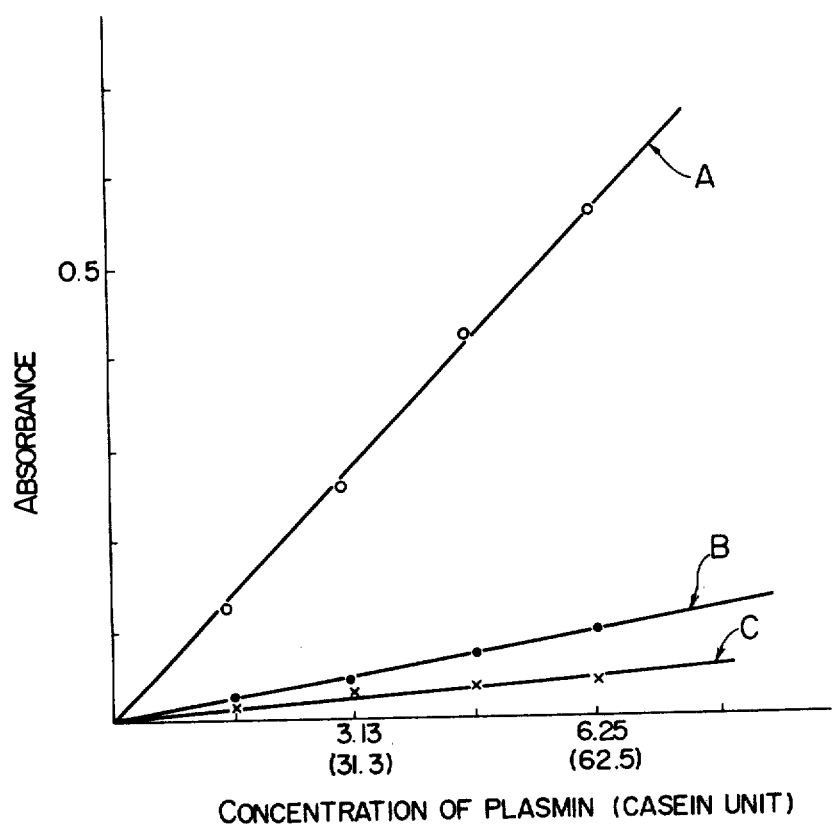

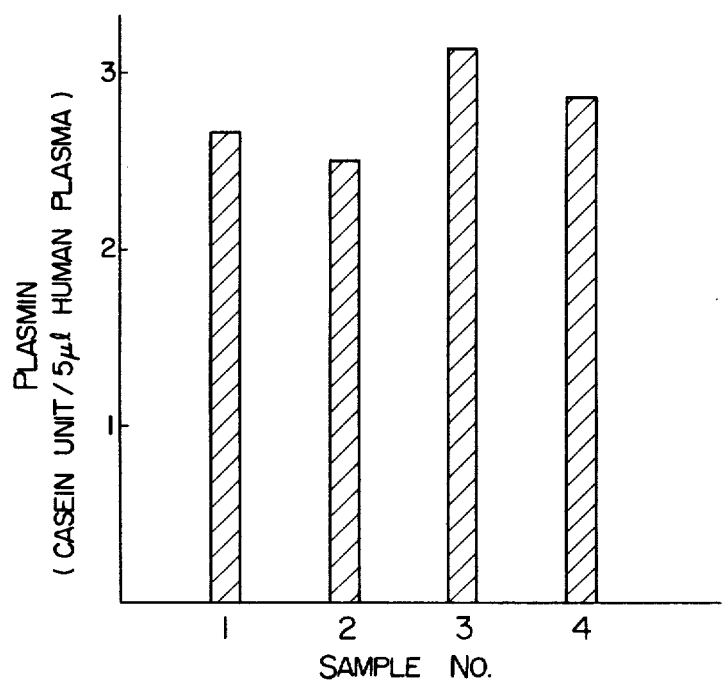

VALYLLEUCYLLYSINE DERIVATIVES, PROCESS FOR PRODUCING SAME AND METHOD FOR MEASURING ACTIVITY OF ENZYMES USING SAME

This invention relates to a novel valylleucyllysine derivative, a process for producing the same, and a method for measuring the activity of enzymes using the compound as a substrate.

Hitherto, many methods have been known for measuring the activity of enzymes. One of them is a method by which an alkyl ester of an amino acid is contacted as a substrate with an enzyme and the activity of the enzyme is determined from the degree of hydrolysis of the alkyl ester. For example, the well-known Hestrin method is one of the methods. This is a method which comprises contacting an enzyme with an alkyl ester of an amino acid, converting the remaining ester group after a given period of time with hydroxylamine into a hydroxamic acid, allowing it to react with ferric chloride to develop a color, and measuring the color as an absorbance, and determining the enzyme's ability to hydrolyze the ester, namely, the activity of enzyme, from the absorbance.

In addition, there is a method in which paranitroanilide of an amino acid is used as a substrate and the ability to hydrolyze the same is used as an index, or the like. In these methods, a considerable amount of an enzyme is required, and when the enzyme concentration is low, or when the enzyme has a low activity, it has been difficult to measure the activity of enzyme.

The present inventors have conducted extensive research on compounds satisfying the following three conditions: They have an affinity to an enzyme, the determination of the amount of enzyme is easy, and the detection sensitivity of the compounds is good. Consequently, the inventors have found compounds useful as substrate which are very excellent as to the above conditions as compared with the conventional ones, and a simple method for measuring the activity of enzyme by use of the compounds.

An object of this invention is to provide a novel amino acid derivative which is useful as an excellent substrate for an enzyme.

Another object of this invention is to provide a process for producing the said novel amino acid derivative.

A further object of this invention is to provide a method for measuring the activity of an enzyme by use of said novel amino acid derivative as a substrate for the enzyme.

Other objects and advantages of this invention will become apparent from the following description.

According to this invention, there is provided a valylleucyllysine derivative represented by the formula,

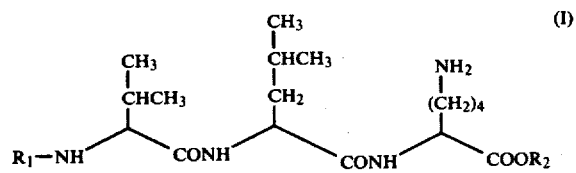

wherein $R_1$ represents hydrogen or benzoyl and $R_2$ represents naphthyl.

This invention further provides a process for producing a valylleucyllysine derivative represented by the formula (I), which comprises subjecting to dehydration-condensation a compound (II) represented by the formula,

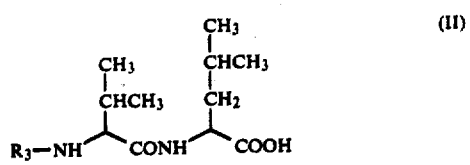

wherein $R_3$ represents benzoyl or an amino-protecting group, and a lysine derivative (III) represented by the formula,

wherein $R_2$ has the same meaning as defined above and $R_4$ represents an amino-protecting group in a conventional manner to obtain a compound (IV) represented by the formula,

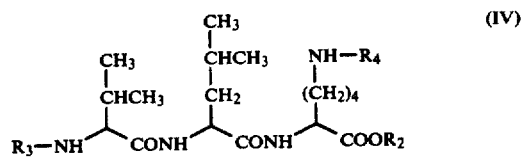

wherein $R_2$, $R_3$ and $R_4$ have the same meanings as defined above, and then removing the amino-protecting group from the compound (IV) in a conventional manner.

According to this invention, there is also provided a method for measuring the activity of an enzyme, which comprises contacting a valylleucyllysine derivative (I) represented by the formula (I) as a substrate with the enzyme.

The starting compound (II) used in the production of the compound (I) of this invention may be prepared by condensing a compound (V) represented by the formula,

wherein $R_3$ has the same meaning as defined above, with a compound (VI) represented by the formula,

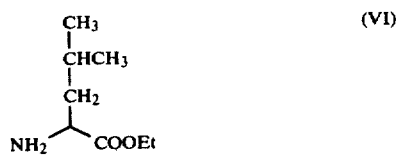

wherein Et means ethyl, into an ester (VII) represented by the formula,

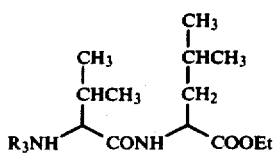

(VII)

wherein $R_3$ and Et have the same meanings as defined above, and then hydrolyzing the ester (VII).

The starting lysine derivative (III) may be prepared by naphthylating a lysine derivative (VIII) having a suitable protecting group represented by the formula,

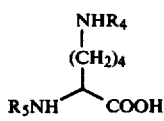

(VIII)

wherein $R_4$ has the same meaning as defined above, and $R_5$ represents an amino-protecting group different from the $R_4$ group, to form a compound (IX) represented by the formula,

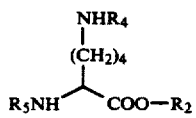

(IX)

wherein $R_2$, $R_4$ and $R_5$ have the same meanings as defined above, and then selectively removing only the amino-protecting group in the α-position from the compound (IX).

In the production of the compound (IV), the compound (II) and the lysine derivative (III) are dissolved in a suitable solvent, and to the resulting solution is added an activating agent which is usually used, such as dicyclohexylcarbodiimide (DCC), diphenylphosphorylazide (DPPA), an alkyl chlorocarbonate or the like, after which, if necessary, a base such as triethylamine or the like is added thereto and the resulting mixture is stirred, thereby preparing the compound (IV). The solvent used includes conventional solvents such as chloroform, dichloromethane, dimethylformamide, tetrahydrofuran and the like as far as the starting materials can be dissolved therein. The reaction temperature may be within the range of 0° to 40° C.

After the completion of the reaction, the compound (IV) can be isolated from the reaction mixture by a conventional treatment. That is to say, when DCC is used as the activating agent, the dicyclohexylurea (DCU) precipitated is removed by filtration, and a suitable extracting solvent such as ethyl acetate is added to the filtrate, after which the extract is washed with an aqueous citric acid solution, saturated aqueous sodium bicarbonate solution and saturated aqueous sodium chloride solution, dried over anhydrous magnesium sulfate, and then evaporated under reduced pressure to remove the solvent to obtain the compound (IV).

The amino-protecting group of the compound (IV) is removed in a conventional manner. That is to say, when the amino-protecting group is benzyloxycarbonyl, the compound (IV) is dissolved in a suitable solvent and a catalyst such as palladium-carbon or the like is added to the resulting solution to remove the protecting group reductively, or the compound (IV) is added to a solution of hydrobromic acid in acetic acid and the hydrobromide of the objective compound precipitated is taken out by filtration, whereby the compound (I) is obtained.

The compound (I) of this invention is useful as an excellent substrate for various enzymes such as trypsin, plasmin, kallikrein, urokinase, Cl-esterase, thrombin and the like. That is to say, when the compound (I) of this invention is contacted with an enzyme, the compound serves as a substrate, and naphthol is liberated by hydrolysis with the enzyme after a given period of time, after which the amount of the naphthol is measured to determine the activity of the enzyme. The fact that the activity of an enzyme can be measured easily is very important for quantitative analysis of an enzyme preparation, diagonosis by measuring the enzyme pattern in blood, diagonosis by measuring the enzyme concentration in blood or urine, or the like.

When the activity of an enzyme is measured according to the process of this invention, the enzyme is contacted with a given amount of the compound (I) of this invention in a suitable buffer solution, and after a given period of time at a given temperature, the amount of naphthol liberated is measured, thereby determining the activity of the enzyme. The buffer solution may be a suitable one having the optimum pH for the enzyme. The reaction may be effected under suitable constant conditions as to temperature and time, though it is preferable to measure the amount of the naphthol liberated at a temperature of 25° to 37° C. after 30 min.

The measurement of the amount of naphthol may be conducted by any of the known methods, for example, a physicochemical method, such as, gas chromatography, thin layer chromatography, or the like; or a chemical method, such as, ferric chloride reaction, diazo-coupling reaction, Fast Violet B salt (FVB) method, or the like, though a method which comprises adding FVB to the reaction mixture to develop a color and measuring the absorbance by means of a photometer is more preferable in view of simplicity and detection sensitivity.

When the activity of plasmin is measured by use of D-valyl-L-leucyl-L-lysine 1-napthyl ester as a substrate, the detection sensitivty thereof is 15 times that of D-valyl-L-leucyl-L-lysine para-nitroanilide which is known as a substrate for the enzyme, and about 62 times that of Nα-tosyl-L-arginine methyl ester.

The amount of the naphthol measured by said method corresponds to the activity or amount of the enzyme.

According to the method of this invention, it is possible to measure the enzyme concentration in blood or urine and to determine the amount of a low active enzyme or an enzyme at a low concentration.

The method for measuring the activity of an enzyme of this invention can be applied to not only a single enzyme-containing system but also a system containing various enzymes. That is to say, the measurement of the enzyme pattern in urine or blood has been interesting for diagonosis of disease, but conventional methods have not been so often conducted because of their complexities. However, with this invention, their complexities have been cleared.

This invention is further illustrated below referring to Example and the accompanying drawings, in which FIG. 1 shows standard curves of the concentration of plasmin, and FIG. 2 is a graph showing the activity of plasmin in human plasma.

EXAMPLE 1

Production of D-valyl-L-leucyl-L-lysine 1-naphthyl ester dihydrochloride

In 10 ml of DMF were dissolved 1.8 g of N-benzyloxycarbonyl-D-valyl-L-leucine and 2.2 g of $N_\epsilon$-benzyloxycarbonyl-L-lysine 1-naphthyl ester hydrochloride, after which 1.3 g of DCC, 0.89 g of 1-hydroxybenzotriazole (HOBt) and 0.7 ml of triethylamine (TEA) were added to the resulting solution with ice-cooling, and then the resulting mixture was stirred for 3 hrs at the same temperature. The mixture was then stirred at room temperature for 24 hrs. After the reaction, the DCU thus precipitated was removed by filtration, and ethyl acetate was added to the filtrate. The resulting mixture was washed with 10% citric acid solution, saturated sodium bicarbonate solution and saturated sodium chloride solution in this order, and thereafter dried over anhydrous magnesium sulfate. The ethyl acetate was removed by evaporation under reduced pressure, and the residue was recrystallized from ethyl acetate to obtain 1.5 g (yield 39%) of white powder of N-benzyloxycarbonyl-D-valyl-L-leucyl-$N_\epsilon$-benzyloxycarbonyl-L-lysine 1-naphthyl ester, m.p. 171°–174° C.

IR $\nu_{max}^{KBr}$ cm$^{-1}$: 3300, 1740, 1680, 1635.

In 10 ml of DMF was dissolved 1.5 g of the above ester, after which 1.0 g of 10% palladium-carbon (Pd-C) and 1.6 g of hydrochloric acid-dioxane solution (110 mg HCl/g) were added. The resulting mixture was stirred at room temperature for 3 hrs while passing hydrogen gas therethrough. After the reaction, the Pd-C was removed by filtration, and 100 ml of anhydrous diethyl ether was added to the filtrate, upon which an oily substance was precipitated. The supernatant was removed by decantation, and the oily substance was washed with diethyl ether, to obtain 0.8 g (yield 73%) of D-valyl-L-leucyl-L-lysine 1-naphthyl ester dihydrochloride.

IR $\nu_{max}^{neat}$ cm$^{-1}$: 2950, 1750, 1650.

The N-benzyloxycarbonyl-D-valyl-L-leucine used as the starting material was produced as follows:

In 250 ml of tetrahydrofuran (THF) were dissolved 54 g of N-benzyloxycarbonyl-D-valine and 39 g of leucine methyl ester hydrochloride, after which 68 g of DPPA and 70 ml of TEA were added to the resulting solution with ice-cooling. The resulting mixture was stirred at room temperature for 24 hrs. The reaction mixture was concentrated under reduced pressure, and ethyl acetate was added to the residue to dissolve the latter. The resulting solution was washed with 10% citric acid solution, saturated sodium bicarbonate solution, and saturated sodium chloride solution in this order, and then distilled under reduced pressure to remove the solvent. The residue was recrystallized from ethyl acetate-n-hexane to obtain 30 g (yield 37%) of colorless needle crystals of N-benzyloxycarbonyl-D-valyl-L-leucine methyl ester, m.p. 112°–114° C.

IR $\nu_{max}^{KBr}$ cm$^{-1}$: 3300, 1730, 1690, 1640.

In 400 ml of methanol was dissolved 30 g of the above ester, and 120 ml of 1 N sodium hydroxide solution was added to the resulting solution, and the resulting mixture was stirred for 3 hrs. After the reaction, the methanol was evaporated under reduced pressure at low temperature, and ethyl acetate was added to the residue and the resulting mixture was shaken. The aqueous layer was made weakly acidic with 10% hydrochloric acid, after which the oily substance thus precipitated was extracted with ethyl acetate. The extract was washed with water, dried over anhydrous magnesium sulfate, and then distilled under reduced pressure to remove the solvent. The residue was recrystallized from ethyl acetate-n-hexane to obtain 19.0 g (yield 66%) of colorless needle crystals of N-benzyloxycarbonyl-D-valyl-L-leucine, m.p. 134°–136° C.

IR $\nu_{max}^{KBr}$ cm$^{-1}$: 3350, 3300, 1730, 1640.

The $N_\epsilon$-benzyloxycarbonyl-L-lysine 1-natphthyl ester hydrochloride used as the starting material was produced as follows:

In a mixed solvent of 25 ml of toluene and 25 ml of pyridine was dissolved 11.4 g of $N\alpha$-t-butoxycarbonyl-$N_\epsilon$-benzyloxycarbonyl-L-lysine, after which 5.2 g of benzenesulfonyl chloride was added to the solution with ice-cooling, and the resulting mixture was stirred at the same temperature for 30 minutes. To the mixture was added 4.2 g of 1-naphthol and the resulting mixture was stirred for 3 hrs, and then stirred at room temperature for 24 hrs. After the reaction, ethyl acetate was added to the reaction mixture, and the mixture was washed with 10% citric acid solution, saturated sodium bicarbonate solution and saturated sodium chloride solution in this order, dried over anhydrous magnesium sulfate, and then evaporated under reduced pressure to remove the solvent, thereby obtaining 13.2 g (yield 87%) of colorless oily substance of $N\alpha$-t-tuboxycarbonyl-$N_\epsilon$-benzyloxycarbonyl-L-lysine 1-naphthyl ester.

IR $\nu_{max}^{neat}$ cm$^{-1}$: 3300, 1750, 1690.

In 25 g of hydrochloric acid-dioxane solution (110 mg HCl/g) was dissolved 13.2 g of the above ester, and the solution was stirred at room temperature for 1.5 hrs. The reaction mixture was evaporated under reduced pressure to dryness, and anhydrous diethyl ether was added to the residue. The resulting mixture was allowed to stand for 24 hrs, and the colorless powders thus precipitated were collected to obtain 11.0 g (yield 95%) of $N_\epsilon$-benzyloxycarbonyl-L-lysine 1-naphthyl ester hydrochloride, m.p. 80°–82° C.

IR $\nu_{max}^{KBr}$ cm$^{-1}$: 3300, 2800, 1750, 1680.

EXAMPLE 2

Production of N-benzoyl-L-valyl-L-leucyl-L-lysine 1-naphthyl ester hydrochloride In 15 ml of DMF were dissolved 1.7 g of N-benzoyl-L-valyl-L-leucine and 2.2 g of $N_\epsilon$-benzyloxy-carbonyl-L-lysine 1-naphthyl ester hydrochloride, after which 1.33 g of DCC, 675 mg of HOBt and 1.0 ml of TEA were added to the solution with ice-cooling, and the resulting mixture was stirred at the same temperature for 3 hrs, and then stirred at room temperature for 24 hrs. After the reaction, the DCU thus precipitated was removed by filtration, and ethyl acetate was added to the filtrate. The resulting mixture was washed with 10% citric acid solution, saturated sodium bicarbonate solution and saturated sodium chloride solution in this order, dried over anhydrous magnesium sulfate, and then evaporated under reduced pressure to remove the solvent. The residue was recrystallized from chloroform-diethyl ether to obtain 1.7 g (yield 41%) of colorless powder of N-benzyl-L-valyl-L-leucyl-$N_\epsilon$-benzyloxycarbonyl-L-lysine 1-naphthyl ester, m.p. 153°–156° C.

IR $\nu_{max}^{KBr}$ cm$^{-1}$: 3300, 1750, 1690, 1630.

In 10 ml of DMF was dissolved 1.4 g of the above ester, after which 0.5 g of 10% Pd-C and 1.0 g of hydrochloric acid-dioxane solution (98 mg HCl/g) were added to the solution. The resulting mixture was stirred at room temperature for 4 hrs while passing hydrogen gas therethrough. After the reaction, the Pd-C was removed by filtration, and 100 ml of anhydrous diethyl ether was added to the filtrate. The white powder thus precipitated was collected to obtain 910 mg (yield 73%) of N-benzoyl-L-valyl-L-leucyl-L-lysine 1-naphthyl ester hydrochloride, m.p. 190°–192° C. (decomp).

IR $\nu_{max}^{KBr}$ cm$^{-1}$: 3300, 2950, 1750, 1630.

The N-benzoyl-L-valyl-L-leucine used as the starting material was produced as follows:

In 100 ml of dichloromethane were dissolved 11.0 g of N-benzoyl-L-valine and 9.0 g of L-leucine ethyl ester hydrochloride, after which 15.0 g of DPPA and 15 ml of TEA were added to the solution with ice-cooling, and the resulting mixture was stirred at the same temperature for 24 hrs. The reaction mixture was washed with 10% citric acid solution, saturated sodium bicarbonate solution and saturated sodium chloride solution in this order, dried over anhydrous magnesium sulfate, and then evaporated under reduced pressure to remove the solvent. The residue was recrystallized from chloroform-diethyl ether-n-hexane to obtain 6.0 g (yield 35%) of colorless needle crystals of N-benzoyl-L-valyl-L-leucine ethyl ester, m.p. 159°–160° C.

IR $\nu_{max}^{KBr}$ cm$^{-1}$: 3300, 3250, 1750, 1630.

In 150 ml of methanol was dissolved 5.0 g of the above ester, and 20 ml of 1N sodium hydroxide solution was added to the solution. The mixture was stirred at room temperature for 8 hrs. The reaction mixture was concentrated at a low temperature, after which ethyl acetate and distilled water were added to the residue. The resulting mixture was shaken, and the aqueous layer was separated and made weakly acidic with 10% hydrochloric acid solution. The oily substance thus precipitated was extracted with ethyl acetate, and the extract was washed with water and dried over anhydrous magnesium sulfate, and thereafter evaporated under reduced pressure to remove the solvent, thereby obtaining 3.0 g (yield 65%) of a colorless oily substance of N-benzoyl-L-valyl-L-leucine.

IR $\nu_{max}^{neat}$ cm$^{-1}$: 3300, 1720, 1630, 2950.

EXAMPLE 3

Measurement of the activity of plasmin by use of D-valyl-L-leucyl-L-lysine 1-naphthyl ester dihydrochloride as substrate.

To 1.7 ml of 50 mM phosphate buffer solution (pH 7.0) were added 0.1 ml of plasmin at various concentrations and 0.2 ml of 1.5 mM D-valyl-L-leucyl-L-lysine 1-naphthyl ester solution, after which the resulting mixture was subjected to incubation at 37° C. for 30 min.

After ice-cooling, 0.1 ml of 1% FVB was added to the mixture, and the mixture was allowed to stand at 0° C. for 10 min, after which 1 ml of glacial acetic acid was further added thereto. The color thus developed was measured as absorbance (505 nm) by a spectrophotometer to determine the amount of the naphthol liberated by hydrolysis with the enzyme. As a control, the buffer solution free from plasmin was used. The amount of the naphthol liberated corresponded to the activity of the enzyme.

When N-benzoyl-L-valyl-L-leucyl-L-lysine 1-naphthyl ester hydrochloride was used as a substrate, the same procedure as above was repeated to measure the activity of the enzyme.

COMPARATIVE EXAMPLE 1

Measurement of the activity of plasmin by use of Nα-tosyl-L-arginine methyl ester hydrochloride as substrate To 0.2 ml of plasmin were added 0.3 ml of Nα-tosyl-L-arginine methyl ester hydrochloride solution (10 micromoles/0.4 ml of 5% DMSO) and 0.5 ml of a borate buffer solution (pH 8.5), and the resulting mixture was subjected to incubation at 37° C. for 30 min, after which 1.5 ml of alkaline hydroxylamine solution (a mixture of equal amounts of 2 M NH$_2$OH hydrochloride and 3.5 M NaOH) was added thereto. The resulting mixture was allowed to stand at room temperature for 15 min. Thereto were added 1 ml of 18% trichloroacetic acid, 1 ml of 4 N hydrochloric acid and 1 ml of 10% ferric chloride solution, and the resulting mixture was thoroughly stirred, after which the mixture was centrifuged at 3,000 r.p.m. for 10 min. The color of the supernatant was measured as absorbance (530 nm) by means of a spectrophotometer. The value thus obtained corresponds to the amount of the substrate remaining unhydrolyzed, and the activity of the enzyme corresponds to the difference between the value obtained when no enzyme was used (control) and the value obtained after the enzyme reaction.

COMPARATIVE EXAMPLE 2

Measurement of the activity of plasmin by use of D-valyl-L-leucyl-L-lysine p-nitroanilide dihydrochloride as substrate To 2.15 ml of 0.1 μM tris HCl buffer solution (pH 8.0) were added 0.1 ml of plasmin at various concentrations and 0.25 ml of D-valyl-L-leucyl-L-lysine p-nitroanilide dihydrochloride solution (1 mM/H$_2$O), and the resulting mixture was subjected to incubation at 37° C. for 30 min. Thereto was added 0.3 ml of glacial acetic acid, and the color developed was measured as absorbance (405 nm) by means of a spectrophotometer.

The results of measurement obtained in Example 3, Comparative Example 1 and Comparative Example 2 are shown in FIG. 1, from which it can be seen that the method of Example 3 has a detection sensitivity about 60 times that of the method of Comparative Example 1 and about 15 times that of the method of Comparative Example 2.

In FIG. 1, curve A is a standard curve obtained by the method of Example 3, curve B is a standard curve obtained by the method of Comparative Example 1 and curve C is a standard curve obtained by the method of Comparative Example 2. The numbers in the parentheses on the abscissa refer to the enzyme concentrations for the curve B.

The following Table indicates the relative sensitivity obtained when the activities of other enzymes were measured by the methods of Example 3 and Comparative Example 2.

TABLE

| Enzyme Substrate | Factor Xa | Kallikrein Plasma | Kallikrein Tissue |
|---|---|---|---|
| D-valyl-L-leucyl-L-lysine 1-napthyl ester dihydrochloride | 30.0 | 30.0 | 8.5 |
| D-valyl-L-leucyl-L-lysine p-nitroanilide dihydro- | 1.0 | 1.0 | 1.0 |

TABLE-continued

| Enzyme | Factor | Kallikrein | |
|---|---|---|---|
| Substrate | Xa | Plasma | Tissue |
| chloride | | | |

EXAMPLE 4

Determination of amount of plasminogen in human plasma

To 5 microliters of citrated human plasma was added 0.8 ml of 50 mM phosphate buffer solution (pH 7.0), and the resulting mixture was thoroughly stirred, after which 0.1 ml of a streptokinase solution (100 units of streptokinase was dissolved in 0.1 ml of 50 mM phosphate buffer solution (pH 7.0) was added thereto. The resulting mixture was subjected to incubation at 37° C. for 30 min, and 0.1 ml of an aqueous solution of a substrate (D-valyl-L-leucyl-L-lysine 1-naphthyl ester dihydrochloride) (0.1 micromole/0.1 ml H₂O) was added thereto to prepare Sample (i). As controls, 0.9 ml of 50 mM of the above phosphate buffer solution and 0.1 ml of the above aqueous solution of substrate were added to 5 microliters of the above citrated human plasma to prepare Sample (ii) and 0.1 ml of the above aqueous solution of substrate was added to 0.9 ml of 50 mM of the above phosphate buffer solution to prepare Sample (iii).

Each of the samples was subjected to incubation at 25° C. for 30 min, and immediately thereafter cooled in iced water, and 0.1 ml of 1% FVB was added thereto. The resulting mixture was allowed to stand for 30 min in iced water, and 1 ml of glacial acetic acid was then added thereto. Within several hours thereafter, the absorbance of each sample was measured at 515 nm, and the amount of the plasminogen in human plasma was calculated by subtracting the total sum of the absorbance of Sample (ii) and the absorbance of Sample (iii) from the absorbance of Sample (i). The amount of plasminogen in the sample is reduced as the plasmin amount from the standard curve (curve A) of human plasmin in FIG. 1 and tabulated. The results of measurement of plasminogen in human plasma according to this method are shown in FIG. 2, in which the plasma samples were obtained from four different men as Sample Nos. 1 to 4.

What is claimed is:

1. A valylleucyllysine derivative represented by the formula,

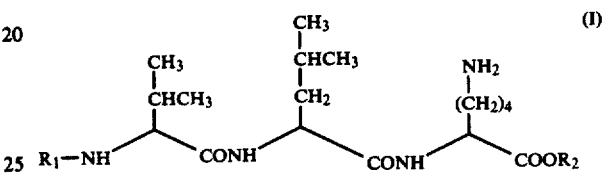

wherein $R_1$ represents hydrogen or benzoyl and $R_2$ represents naphthyl.

2. D-valyl-L-leucyl-L-lysine 1-naphthyl ester.

3. N-benzoyl-L-valyl-L-leucyl-L-lysine 1-naphthyl ester.

* * * * *